(12) United States Patent
Boschert

(10) Patent No.: US 7,857,834 B2
(45) Date of Patent: Dec. 28, 2010

(54) SPINAL IMPLANT FIXATION ASSEMBLY

(75) Inventor: Paul F. Boschert, Minneapolis, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 0 days.

(21) Appl. No.: 10/874,785

(22) Filed: Jun. 14, 2004

(65) Prior Publication Data
US 2005/0277928 A1 Dec. 15, 2005

(51) Int. Cl.
*A61B 17/70* (2006.01)
(52) U.S. Cl. .................. 606/269; 606/266
(58) Field of Classification Search ............ 606/61, 606/73, 250–279, 287, 300–331
See application file for complete search history.

(56) References Cited

U.S. PATENT DOCUMENTS

| | | | |
|---|---|---|---|
| 5,024,213 A | 6/1991 | Asher et al. | |
| 5,129,388 A | 7/1992 | Vignaud et al. | |
| 5,129,900 A * | 7/1992 | Asher et al. | 606/264 |
| 5,257,993 A | 11/1993 | Asher et al. | |
| 5,443,467 A | 8/1995 | Biedermann et al. | |
| 5,476,464 A | 12/1995 | Metz-Stavenhagen et al. | |
| 5,487,744 A * | 1/1996 | Howland | 606/61 |
| 5,628,740 A | 5/1997 | Mullane | |
| 5,662,650 A * | 9/1997 | Bailey et al. | 606/59 |
| 5,669,911 A * | 9/1997 | Errico et al. | 606/264 |
| 5,672,176 A | 9/1997 | Biedermann et al. | |
| 5,733,286 A | 3/1998 | Errico et al. | |
| 5,782,833 A | 7/1998 | Haider | |
| 5,879,350 A | 3/1999 | Sherman et al. | |
| 5,882,350 A * | 3/1999 | Ralph et al. | 606/278 |
| 5,885,286 A | 3/1999 | Sherman et al. | |
| 5,954,725 A * | 9/1999 | Sherman et al. | 606/78 |
| 5,964,760 A * | 10/1999 | Richelsoph | 606/279 |
| 6,010,503 A * | 1/2000 | Richelsoph et al. | 606/278 |
| 6,053,917 A * | 4/2000 | Sherman et al. | 606/61 |
| 6,063,090 A | 5/2000 | Schlapfer | |
| 6,074,391 A | 6/2000 | Metz-Stavenhagen et al. | |

(Continued)

FOREIGN PATENT DOCUMENTS

EP 0 786 235 B1 7/1997

(Continued)

OTHER PUBLICATIONS

Exhibit A: Three views of the Xia™ Pedicle Screw from Stryker Hownedica Osteonics (Date: This art was known prior to filing of present U.S. Appl. No. 10/874,785.).

*Primary Examiner*—Thomas C Barrett
*Assistant Examiner*—Larry E Waggle
(74) *Attorney, Agent, or Firm*—Seager, Tufte & Wickhem, LLC

(57) ABSTRACT

An orthopedic fixation device for securing a rod to a bone is provided. The fixation device includes a receiver with two legs, a pocket defined between the legs, an anchor including a head, and a seat structure that mounts within the receiver. The seat structure includes a top seat for receiving the rod and a bottom seat for receiving the head of the anchor. The top seat includes two legs defining a pocket and first and second raised ridges that are spaced apart from one another. The legs each define a recessed portion extending between the two raised ridges.

19 Claims, 16 Drawing Sheets

U.S. PATENT DOCUMENTS

| | | | |
|---|---|---|---|
| 6,077,262 A | 6/2000 | Schlapfer et al. | |
| 6,113,601 A | 9/2000 | Tatar | |
| 6,146,383 A * | 11/2000 | Studer et al. | 606/308 |
| 6,248,105 B1 | 6/2001 | Schlapfer et al. | |
| 6,280,442 B1 * | 8/2001 | Barker et al. | 606/60 |
| 6,355,040 B1 | 3/2002 | Richelsoph et al. | |
| 6,371,957 B1 | 4/2002 | Amrein et al. | |
| 6,440,137 B1 * | 8/2002 | Horvath et al. | 606/73 |
| 6,471,705 B1 * | 10/2002 | Biedermann et al. | 606/61 |
| 6,488,681 B2 | 12/2002 | Martin et al. | |
| 6,835,196 B2 * | 12/2004 | Biedermann et al. | 606/308 |
| 7,087,057 B2 * | 8/2006 | Konieczynski et al. | 606/278 |
| 2002/0133154 A1 | 9/2002 | Saint Martin | |
| 2002/0143341 A1 | 10/2002 | Biedermann et al. | |
| 2002/0173791 A1 * | 11/2002 | Howland | 606/61 |
| 2003/0023243 A1 | 1/2003 | Biedermann et al. | |
| 2003/0100896 A1 | 5/2003 | Biedermann et al. | |
| 2003/0100904 A1 | 5/2003 | Biedermann | |
| 2003/0114852 A1 | 6/2003 | Biedermann et al. | |
| 2003/0125741 A1 | 7/2003 | Biedermann et al. | |
| 2003/0158552 A1 * | 8/2003 | Jeon et al. | 606/61 |
| 2003/0187433 A1 | 10/2003 | Lin | |
| 2003/0199873 A1 | 10/2003 | Richelsoph | |
| 2004/0176766 A1 * | 9/2004 | Shluzas | 606/65 |
| 2006/0089643 A1 * | 4/2006 | Mujwid | 606/61 |

FOREIGN PATENT DOCUMENTS

| | | |
|---|---|---|
| EP | 1 402 828 A1 | 3/2004 |
| FR | 2 794 637 A1 | 12/2000 |
| WO | WO 03/068083 A1 | 8/2003 |
| WO | WO 2005/018471 A1 | 3/2005 |

* cited by examiner

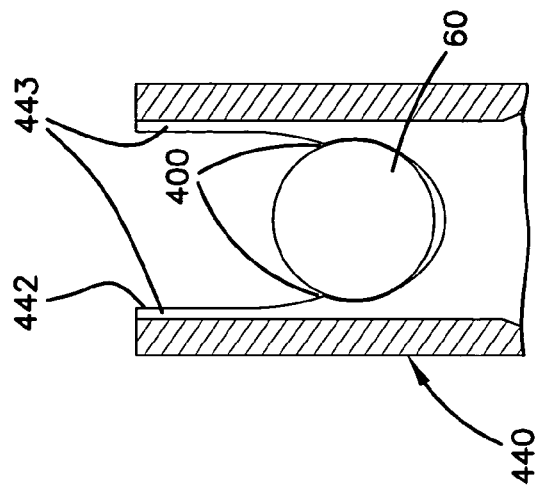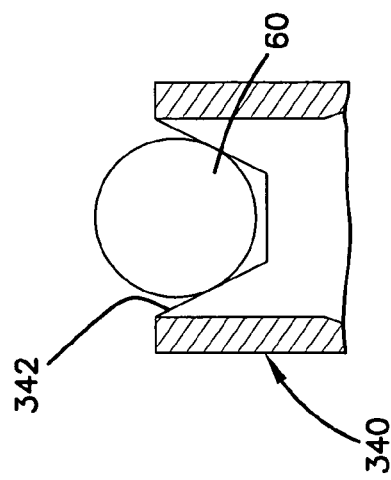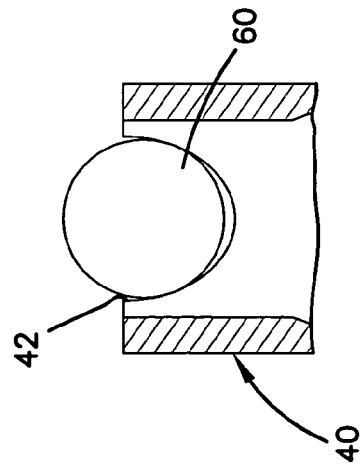

US 7,857,834 B2

SPINAL IMPLANT FIXATION ASSEMBLY

TECHNICAL FIELD

This invention pertains to vertebral stabilization. Specifically, the invention provides intervertebral connection systems suited for stabilization of the spine.

BACKGROUND

The spinal column is a highly complex system of bones and connective tissues that provides support for the body and protects the delicate spinal cord and nerves. The spinal column includes a series of vertebrae stacked one atop the other, each vertebral body including an inner or central portion of relatively weak cancellous bone and an outer portion of relatively strong cortical bone. Situated between each vertebral body is an intervertebral disc that cushions and dampens compressive forces experienced by the spinal column. A vertebral canal containing the spinal cord and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

The present invention generally involves a technique commonly referred to as spinal fixation whereby surgical implants are used for fusing together and/or mechanically immobilizing vertebrae of the spine. Spinal fixation may also be used to alter the alignment of adjacent vertebrae relative to one another so as to change the overall alignment of the spine. Such techniques have been used effectively to treat the above-described conditions and, in most cases, to relieve pain suffered by the patient. However, as will be set forth in more detail below, there are some disadvantages associated with current fixation devices.

One spinal fixation technique involves immobilizing the spine by using orthopedic rods, commonly referred to as spine rods, that run generally parallel to the spine. This may be accomplished by exposing the spine posteriorly and fastening bone screws to the pedicles of the appropriate vertebrae. Clamping elements adapted for receiving a spine rod therethrough are then used to join the spine rods to the screws. The aligning influence of the rods forces the spine to conform to a more desirable shape. In certain instances, the spine rods may be bent to achieve the desired curvature of the spinal column. Some examples of such spinal stabilization systems are disclosed in U.S. Pat. Nos. 6,074,391; 6,488,681; 6,280,442; 5,879,350; 6,371,957 B1; 6,355,040; 5,882,350; 6,248,105; 5,443,467; 6,113,601; 5,129,388; 5,733,286; 5,672,176; and 5,476,464, the entire disclosures of which are incorporated herein by reference.

U.S. Pat. No. 5,129,388 to Vignaud et al. discloses a spinal fixation device including a pedicle screw having a U-shaped head rigidly connected to an upper end of the screw. The U-shaped head includes two arms forming a U-shaped channel for receiving a spine rod therein. The U-shaped head is internally threaded so that a set screw having external threads may be screwed therein. After the pedicle screw has been inserted into bone and a spine rod positioned in the U-shaped channel, the set screw is threaded into the internal threads of the U-shaped channel for securing the spine rod in the channel and blocking relative movement between the spine rod and the pedicle screw.

Surgeons have encountered considerable difficulty when attempting to insert spinal fixation devices such as those disclosed in the above-mentioned '388 patent. This is because the U-shaped heads of adjacent screws are often out of alignment with one another due to curvature in spines and the different orientations of the pedicles receiving the screws. As a result, spine rods must often be bent in multiple planes in order to pass the rods through adjacent U-shaped channels. These problems weaken the strength of the assembly and result in significantly longer operations, thereby increasing the likelihood of complications associated with surgery.

In response to the above-noted problems, U.S. Pat. No. 5,733,286 to Errico et al., U.S. Pat. No. 5,672,176 to Biedermann et al., and U.S. Pat. No. 5,476,464 to Metz-Stavenhagen disclose polyaxial spinal fixation devices wherein the anchoring element fixed to the bone has a spherically-shaped head. The fixation devices in the above-identified patents also have orthopedic rod capturing assemblies for securing orthopedic rods in the capturing assemblies and connecting the rods with the anchoring elements. The spherically shaped heads of the anchoring elements permit movement of the anchoring elements relative to the orthopedic rod capturing assemblies.

There is a need for a screw head securing mechanism or device that provides a strong, effective, and secure lock of the screw head in its desired position. Additionally, there is a need for a screw head securing mechanism or device that is minimal in size and has a reduced amount of components to provide for a simpler, more effective, and less cumbersome device for fixing screws. Moreover, there is a need for a device adapted to more easily receive curved rods.

SUMMARY

One inventive aspect of the disclosure relates to providing orthopedic fixation systems for securing a rod to a bone with means for receiving curved rods.

Another inventive aspect of the disclosure relates to orthopedic fixation systems that secure polyaxial anchors by providing substantially full rings of contact with the heads of the anchors regardless of the angular orientations of the anchors.

Yet another aspect of the disclosure relates to providing orthopedic fixation systems for securing a rod to a bone including receivers and seat structures mounted within the receivers, wherein the receivers and the seat structures include relative anti-rotation features.

It should be noted that, at various locations throughout the specification, guidance is provided through lists of examples. The examples are for illustrative purposes and are not intended to limit the scope of the invention.

BRIEF DESCRIPTION OF THE DRAWINGS

FIG. 18 is a cross-sectional view of the seat of orthopedic fixation device of FIG. 1 showing the rod seated at the top side of the seat;

FIG. 19 is a cross-sectional view of another embodiment of a seat having features that are examples of inventive aspects disclosed herein, the seat has a modified top side for seating the rod;

FIG. 20 is a cross-sectional view of another embodiment of a seat having features that are examples of inventive aspects disclosed herein, the seat includes tabs for provisionally retaining the rod at the top of the seat;

DETAILED DESCRIPTION

The invention will now be described by reference to the several drawing figures. The functional features of the invention can be embodied in any number of specific configurations. It will be appreciated, however, that the illustrated embodiments are provided for descriptive purposes and should not be used to limit the invention.

Figure 1:
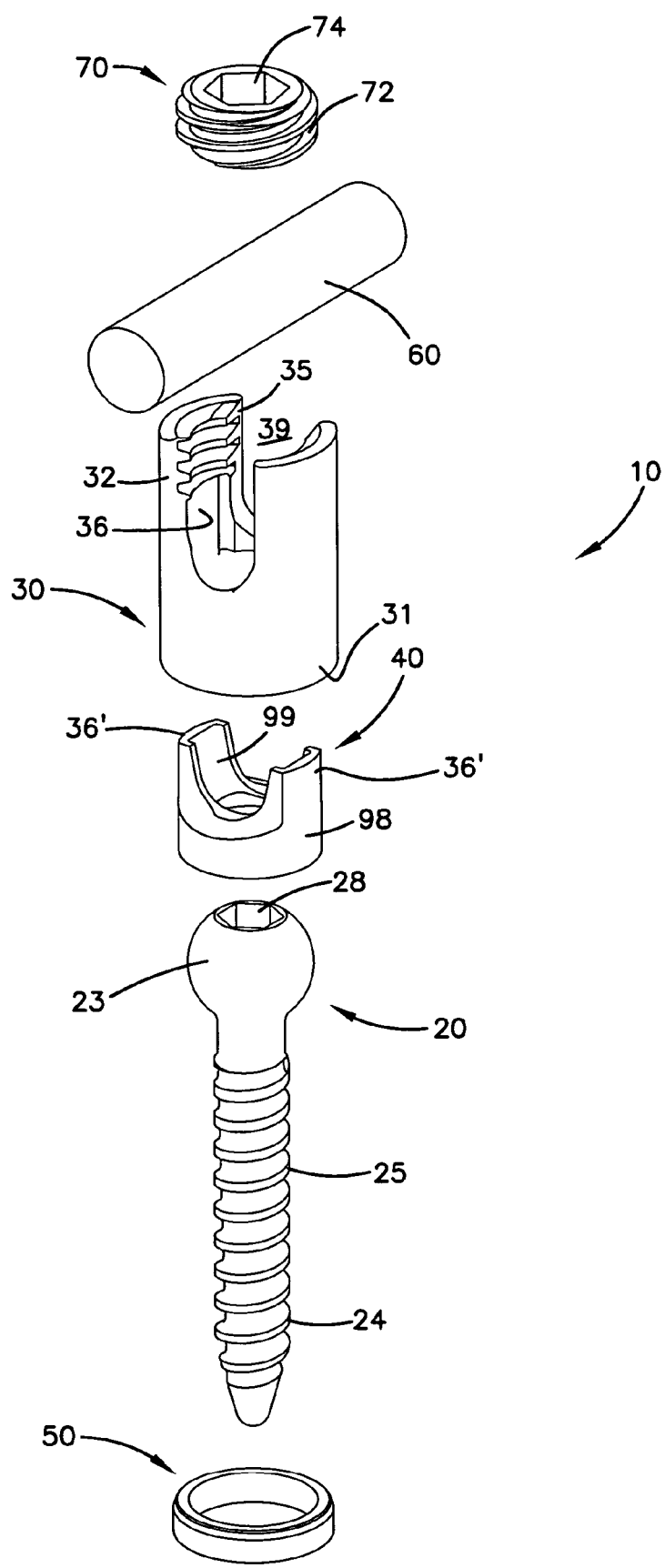
FIG. 1 is an exploded perspective view of an orthopedic fixation device having features that are examples of inventive aspects in accordance with the principles of the present disclosure.

FIG. 1 illustrates one embodiment of an orthopedic fixation device 10 having features that are examples of inventive aspects in accordance with the principles of the present disclosure. The fixation device 10 includes a receiver 30 having a top portion 32 defining a saddle 39 (i.e., a pocket) for receiving a rod 60, and a bottom portion 31 adapted for receiving a head 23 of a bone fastener such as a bone screw 20. The fixation device 10 also includes a seat structure 40 that mounts within the receiver 30 between the rod 60 and the head 23 of the screw 20. The seat structure 40 and the head 23 of the screw 20 are bottom loaded into the bottom portion 31 of the receiver 30, and then captured within the receiver 30 by a retainer 50 (e.g., a retaining ring) secured to the bottom end of the receiver 30. The fixation device 10 further includes a fastener such as a setscrew 70 for clamping the rod 60 within the saddle 39 of the receiver 30.

Figure 2:
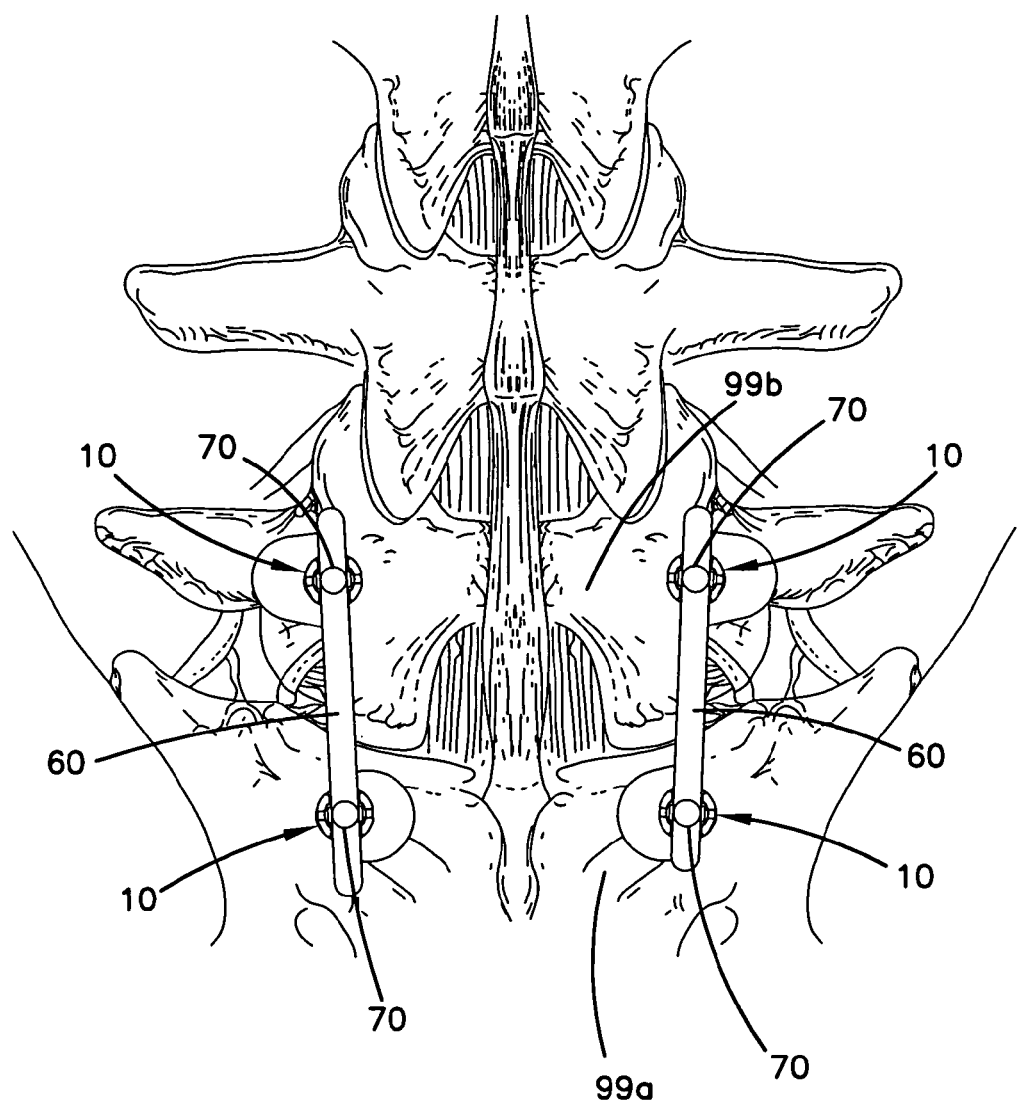
FIG. 2 is a top plan view of a stabilization construct including fixation devices of the type shown in FIG. 1, the stabilization construct is shown mounted on the vertebrae from a posterior approach.

In general use, a plurality of the fixation devices 10 are anchored to bones such as vertebral bodies 99a, 99b (shown at FIG. 2) desired to be stabilized. The fixation devices can be anchored to the vertebral bodies 99a, 99b by threading the bone screws 20 into the vertebral bodies 99a, 99b. Torque for driving the screws 20 can be provided by a tool (e.g., a torque wrench or screw driver) inserted through the receivers 30 and into sockets 28 (e.g., hex-sockets) provided in the heads 23 of the screws 20. By threading the screws 20 into the vertebral bodies 99a, 99b, the screws 20 function to couple the receivers 30 to the vertebral bodies 99a, 99b as shown at FIG. 2. After coupling the receivers 30 to the vertebral bodies 99a, 99b with the screws, the vertebral bodies 99a, 99b can be distracted apart, compressed together or otherwise moved to a desired relative positioning. Rods 60 can then be mounted within the receivers 30 as shown in FIG. 2. The polyaxial configuration of the bone screws 20 allow the receivers 30 to pivot relative to the bone screws 20 to facilitate inserting the rods 60 in the saddles 39 of the receivers 30. Once the rods 60 are inserted within the receivers 30, the setscrews 70 are threaded into the saddles 39 thereby forcing the rods 60 to seat against the top sides of the seat structures 40. Continued tightening of the setscrews 70 forces the seat structures 40 downwardly within the receivers 30 causing the heads 23 of the bone screws 20 to be clamped between the bottom sides of the seat structures 40 and the retainers 50, and also causing the rods 60 to be clamped between the setscrews 70 and the top sides of the seat structures 40. The rods 60 are preferably clamped with sufficient force to prevent the rods 60 from sliding relative to the receivers 30, and the screw heads 23 are preferably clamped with sufficient force to prevent the screw heads 23 from pivoting relative to the receivers 30. In this manner, the rods 60 and the fixation devices 10 cooperate to form a stabilizing construct or framework that braces the vertebral bodies 99a, 99b to maintain the desired spatial relationship between the vertebral bodies 99a, 99b.

Referring to FIG. 1, the screw 20 of the fixation device 10 includes a bone engaging end 24 and a generally spherical head 23. The bone-engaging end 24 preferably includes external threads 25 adapted to allow the screw 20 to be screwed into bone material. The spherical head 23 includes a major diameter 26 sized such that the spherical head 23 can be loaded into the receiver 30 from the bottom end of the receiver 30. The spherical head 23 is shaped to allow a polyaxial freedom of movement for the screw 20. In this manner, the screw 20 can have a range of motion throughout a 360-degree pattern from a longitudinal axis of the receiver 30. Polyaxial freedom of movement of the screw 20 provides the surgeon with a wide range of placement angles, thereby facilitating the rod placement process.

Figure 6:
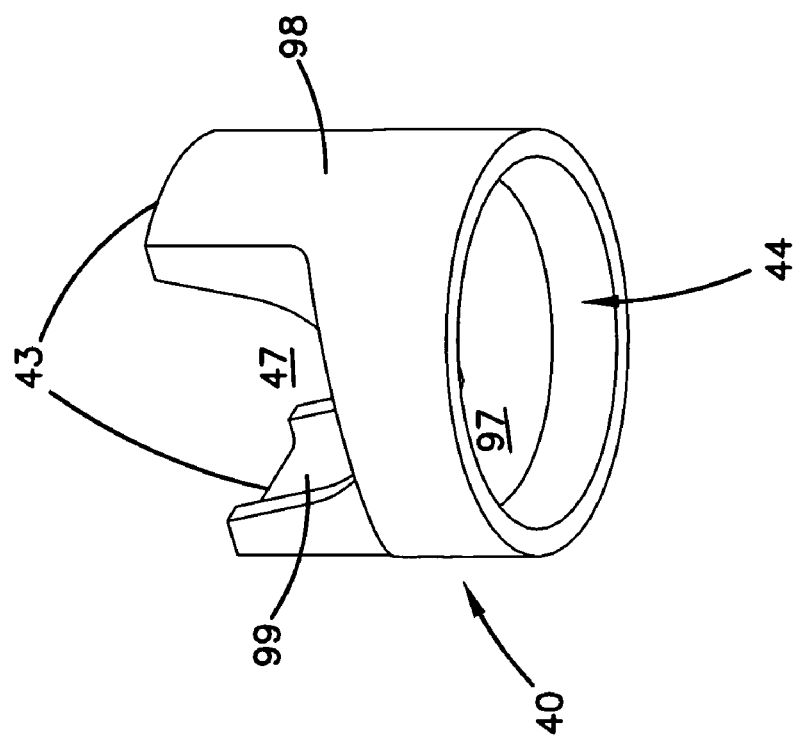
FIG. 6 is a bottom, perspective view of the seat structure of the orthopedic fixation device of FIG. 1.
Figure 5:
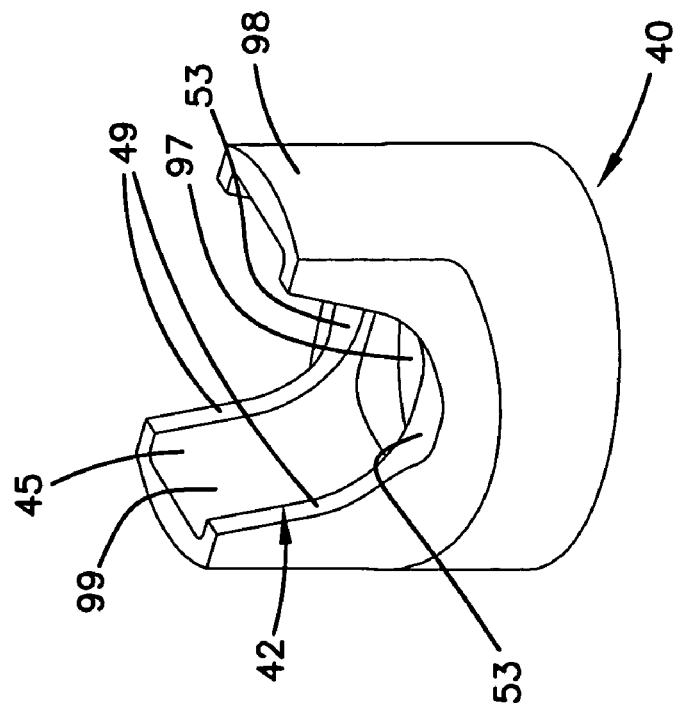
FIG. 5 is a top, perspective view of a seat structure of the orthopedic fixation device of FIG. 1.
Figure 7:
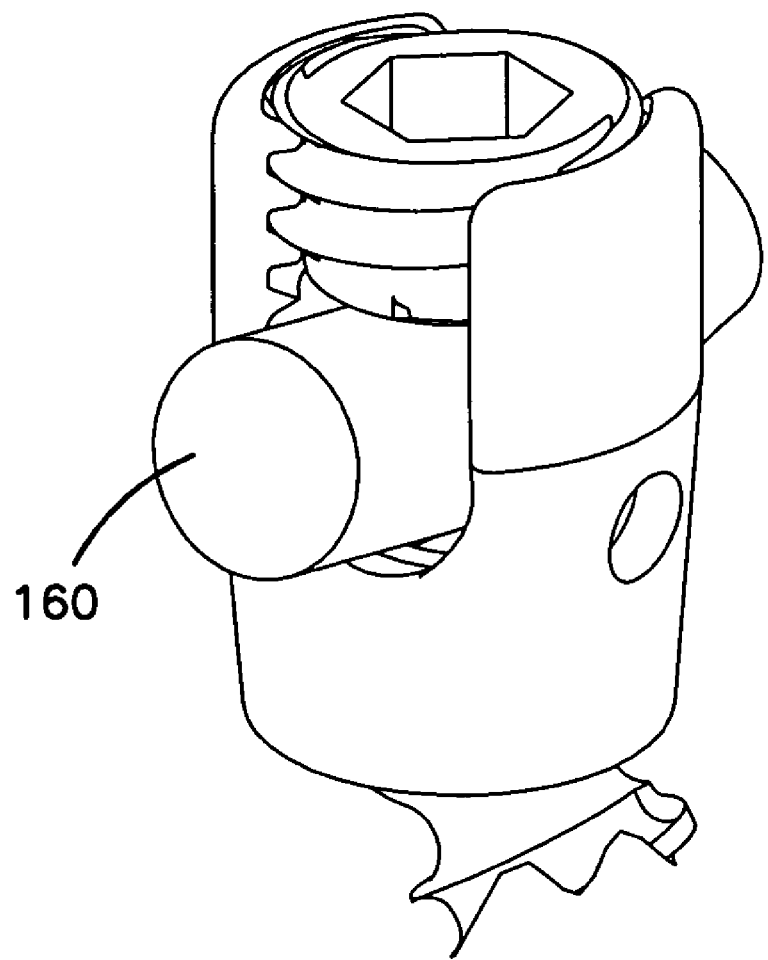
FIG. 7 is a perspective view of the orthopedic fixation device of FIG. 1 with a bent rod secured therein, the rod has an anterior-posterior curvature.
Figure 10:
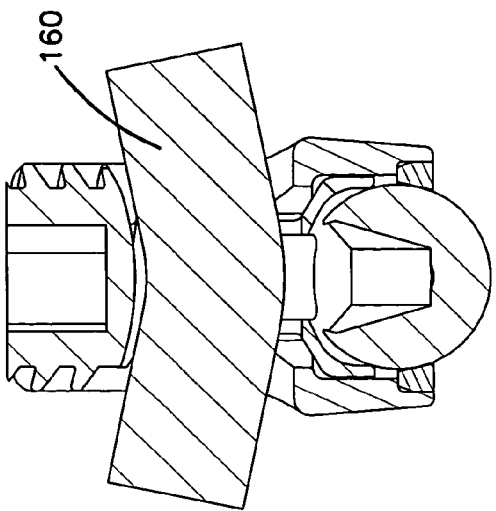
FIG. 10 is a cross-sectional view taken along section line 10-10 of FIG. 8.
Figure 9:
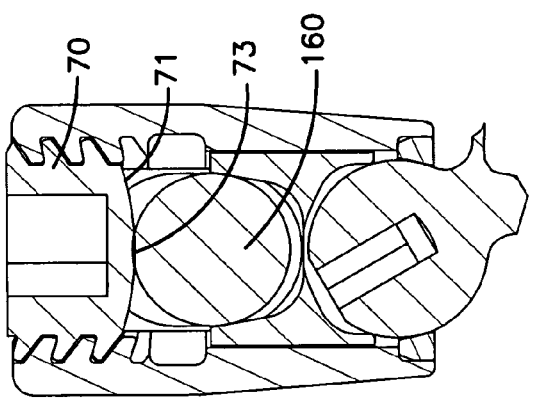
FIG. 9 is a cross-sectional view taken along section-line 9-9 of FIG. 8.
Figure 8:
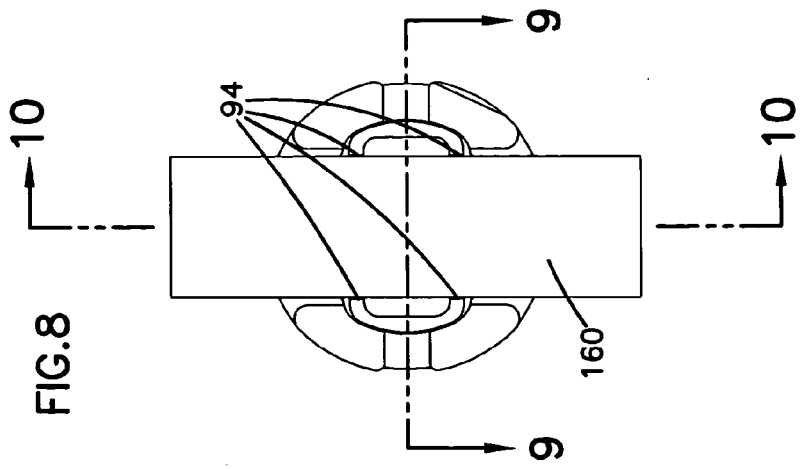
FIG. 8 is a top view of the orthopedic fixation device of FIG. 7 with the locking plug removed to better depict the interior of the receiver.

FIGS. 5 and 6 are perspective views of the seat structure 40 of the orthopedic fixation device of FIG. 1. The seat structure 40 includes a top seat 42 for receiving the rod 60, a bottom seat 44 for receiving the head 23 of the screw 20 and a through-hole 97 communicating between the top seat 42 and the bottom seat 44. The seat structure 40 also includes an exterior surface 98 and an interior surface 99. The seat structure 40 is shaped and sized to be inserted into the receiver 30 through the bottom end of the receiver 30.

The top seat 42 of the seat structure 40 includes two legs 43 defining a pocket 47. The top seat 42 also includes first and second raised rod contacting structures such as ridges 49 that are spaced apart from one another. Each of the legs 43 defines a recessed portion 45 in the interior surface 99 extending between the two ridges 49.

Figure 3:
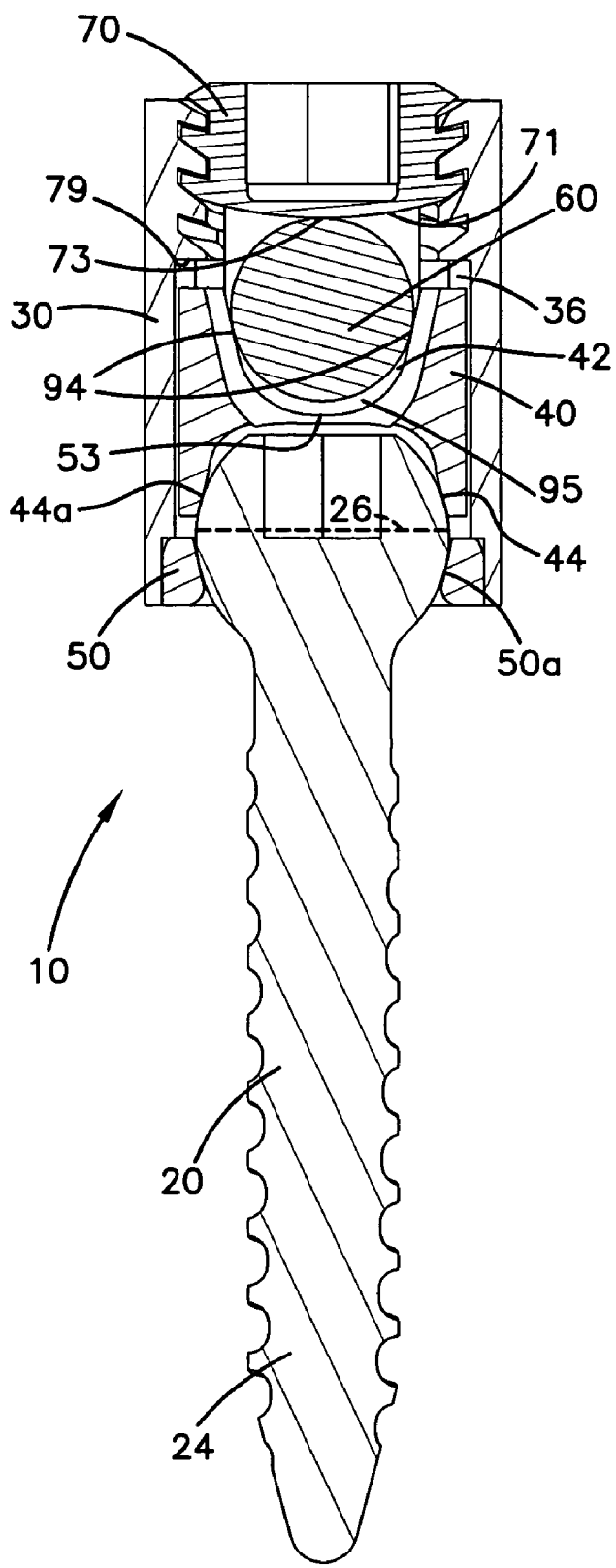
FIG. 3 is a cross-sectional view of the orthopedic fixation device of FIG. 1 taken along a vertical cross-sectional plane that bisects the device, the device is shown with a rod in a locked position within a receiver of the device.
Figure 4:
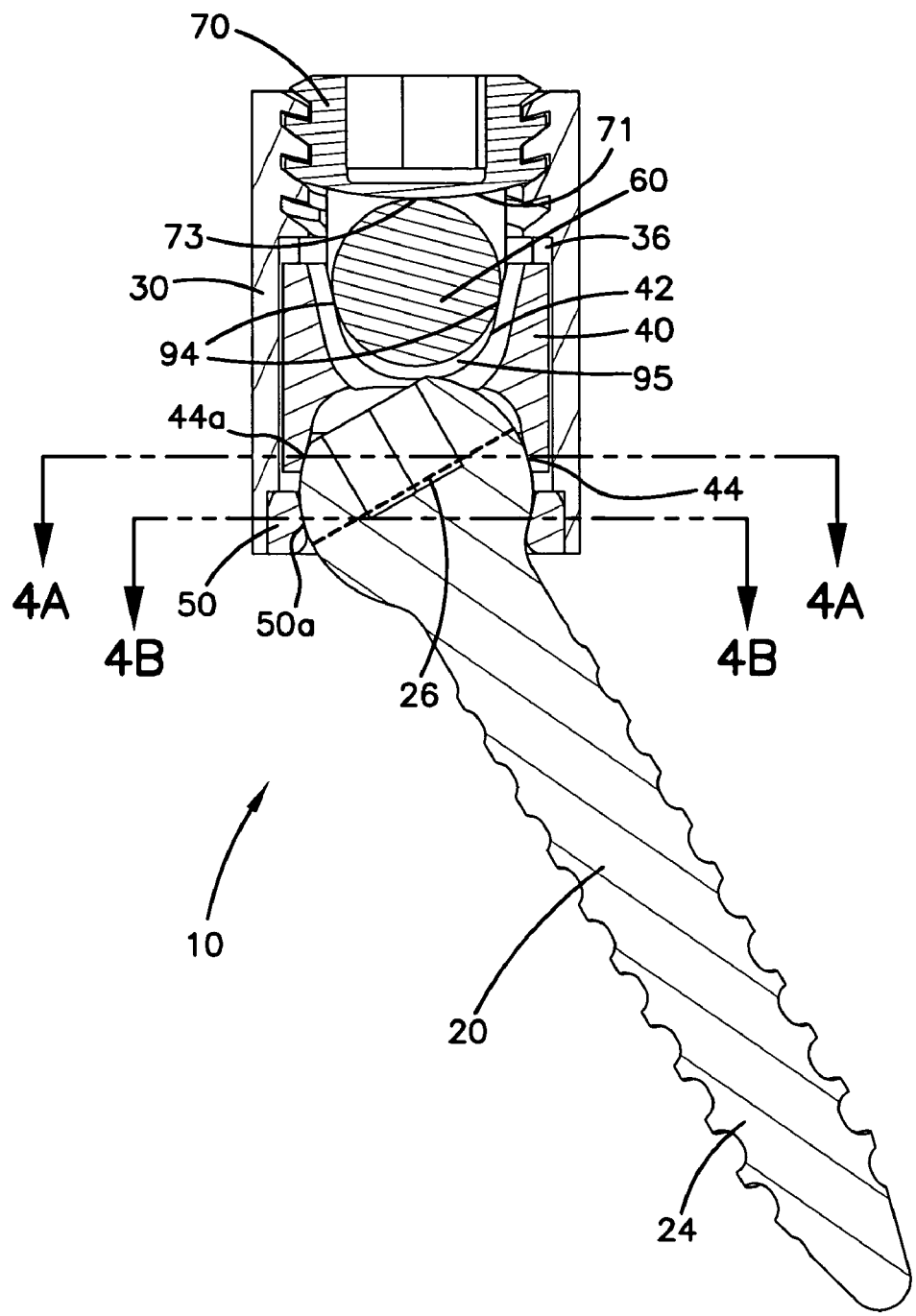
FIG. 4 is another cross-sectional view of the orthopedic fixation device of FIG. 1 showing the polyaxial anchor at an angled orientation relative to the receiver.

As illustrated in FIGS. 3 and 4, each of the ridges 49 provides two contact locations 94 on the sides of the rod 60. Non-contact areas 95 are defined between the bottom of the rod 60 and the bottom 53 of the pocket 47. The non-contact areas 95 are provided by sizing the rod radius of curvature larger than the pocket radius of curvature.

Figure 11:
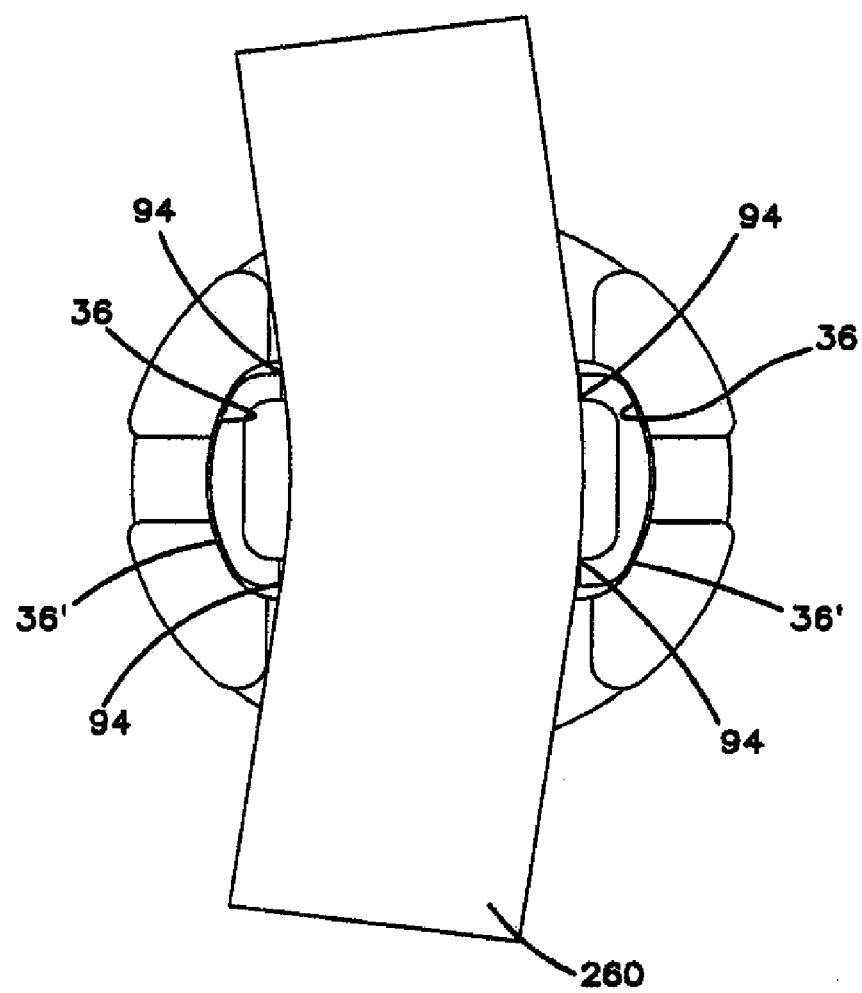
FIG. 11 is a top view of the orthopedic fixation device of FIG. 1 with a bent rod mounted therein, the bent rod has a lateral curvature.

The non-contact area 95, the recessed portions 45 between the ridges 49 and the location of the through-hole 97 are configured to facilitate seating of the bent rods by providing open regions for accommodating the curvatures of the rods. FIGS. 7-10 show a rod 160 having an anterior-posterior curvature. Means for accommodating this curvature while maintaining secure contact is provided by the ridges 49 and the clearance provided by the non-contact areas 95 and the through hole 97 between the ridges. FIG. 11 shows a rod 260 having a lateral curvature. Means for accommodating this curvature while maintaining secure contact is provided by the ridges 49 and the recessed portions 45 between the ridges 49. As shown at FIG. 11, the ridges provide four discrete contact locations 94 while the recessed portions 45 provide clearance for accommodating the lateral curvature of the rod.

The rod contacting structures 49 are adapted to form four separate contact areas 94 with a rod regardless of which way the rod has been bent. In this manner, the rod contacting structures 49 provide stability to any rod that has been seated on the top seat 42 regardless of the rod's curvature. Corrective manipulations may be done to the rod while the rod is at rest on the top seat 42.

As shown in FIGS. 5 and 6, the bottom seat 44 of the seat structure 40 is adapted to receive the head 23 of the screw 20. After the seat structure 40 has been inserted within the receiver 30, the bottom seat 44 is adapted to contact the spherical head 23 of the screw 20 when the screw 20 is inserted within the receiver 30 from the bottom end of the receiver 30.

Figure 4A:
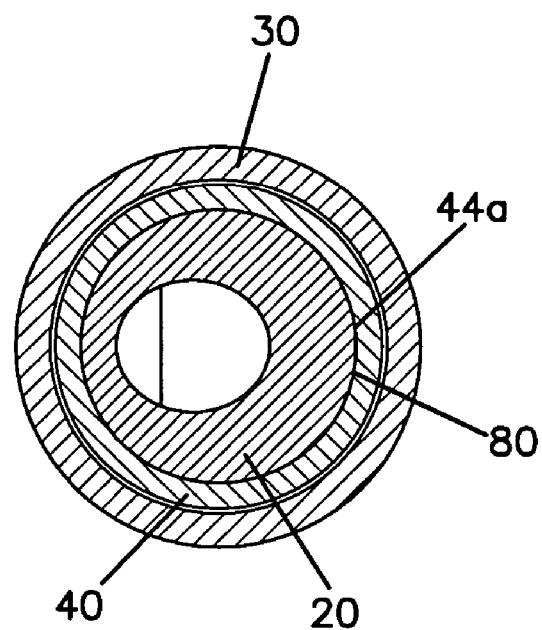
FIG. 4A is a cross-sectional view of the orthopedic fixation device of FIG. 1 taken along section-line 4A-4A of FIG. 4.

The bottom seat 44 of the seat structure includes an annular seating surface 44a having a curvature that generally matches the curvature of the exterior surface of the head 23 of the screw 20. The seating surface 44a faces in a generally downward direction and is adapted to provide a full ring of contact 80 (shown in FIG. 4A) with the head 23 throughout the range of pivotal movement of the screw 20 relative to the receiver 30. When the fixation device is tightened as shown in FIGS. 3 and 4, the seating surface 44a presses down on the screw head 23 to clamp the screw at the desired angular position. During the clamping process, the surface 44a maintains the substantially full ring contact 80 with the spherical head 23 of the screw 20 regardless of the angular orientation of the screw 20 relative to the receiver 30 such that the screw is securely clamped at the desired angular orientation relative to the receiver 30.

Figure 12:
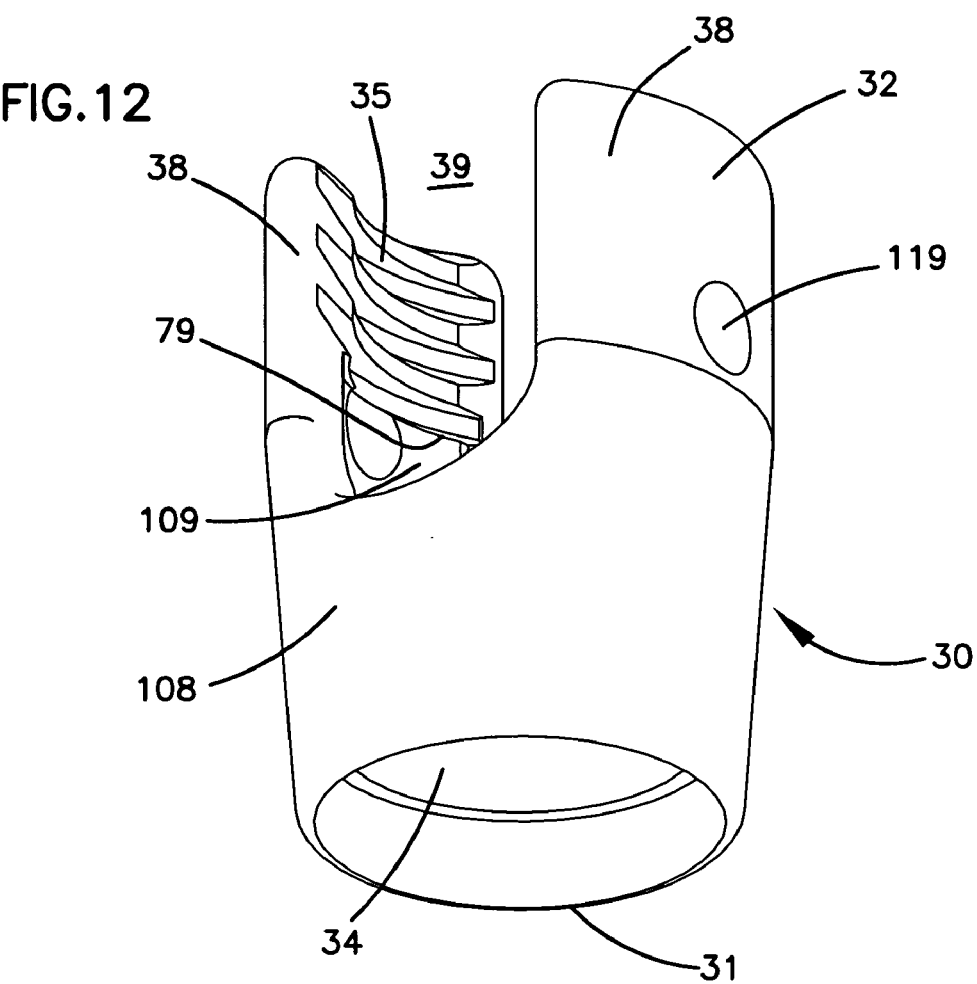
FIG. 12 is a bottom, perspective view of a receiver of the orthopedic fixation device of FIG. 1.

FIG. 12 illustrates the receiver 30 of the orthopedic fixation device 10 of FIG. 1. The receiver 30 includes an outer surface 108, and an inner surface 109. The receiver 30 also includes a throughhole 34 extending vertically from the top portion 32 to the bottom portion 31 of the receiver 30. As illustrated in FIG. 12, the receiver 30 may also include grasping features 119 on the outer surface 108 that would accommodate instrumentation to facilitate grasping, holding or manipulating of the receiver 30.

The receiver 30 includes two upwardly extending legs 38 between which the saddle 39 of the receiver 30 is defined. The saddle 39 of the receiver 30 provides an open region or pocket for receiving the rod 60. The legs 38 also preferably include fastening structure for interconnecting with the setscrew 70. For example, the legs 38 are shown defining interior threads 35 that mate with corresponding exterior threads 72 of the setscrew 70 to allow the setscrew 70 to be threaded into the saddle 39 to lock the rod 60 and screw in place.

The seat structure 40 is configured to be bottom-loaded into the receiver 30. When the seat structure 40 is bottom-loaded into the receiver 30, the seat structure 40 is prevented from being pushed upwardly through the top end of the receiver 30 by a stop structure 79.

The receiver 30 may include a keying feature 36 for aligning the seat structure 40 in the correct rotational orientation relative to the receiver 30 during insertion. The keying structure 36 can also limit rotation of the seat structure 40 relative to the receiver 30 once inserted. As used herein, the term "limit" can mean either prevent rotation or limit rotation to a certain range. In FIG. 1, the keying feature 36 is depicted as opposing internal slots 36 defined along the inner surface 109. The internal slots 36 have generally rectangular shapes and are configured to complement and receive corresponding rectangular shape structures 36' provided at the exterior 98 of the seat structure 40. The internal slots 36 are used to align the pockets 47 of the seat structure 40 with the saddle 39 of the receiver 30. It will be understood that other types of keying features (e.g., tabs, notches, polygonal shapes, slots, flats, or other structures) can be utilized to correctly align the seat structure relative to the receiver within the spirit of the invention.

Figure 4B:
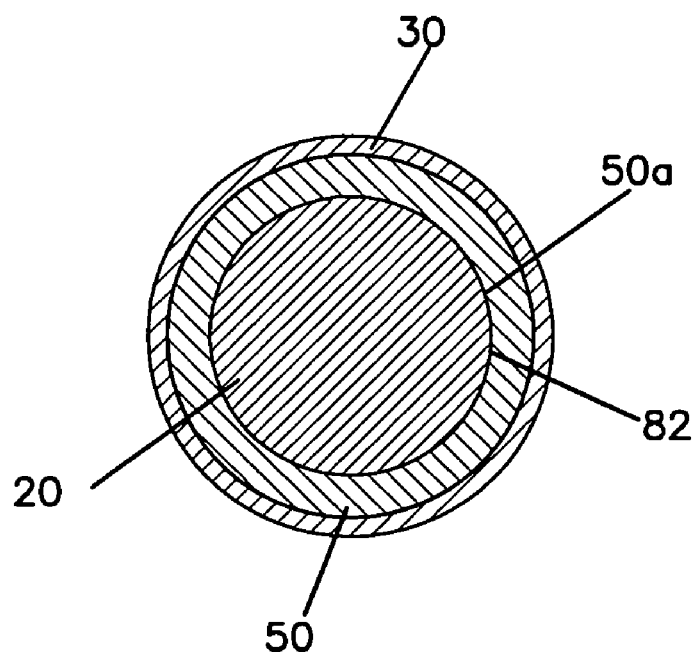
FIG. 4B is a cross-sectional view of the orthopedic fixation device of FIG. 1 taken along section-line 4B-4B of FIG. 4.
Figure 13:
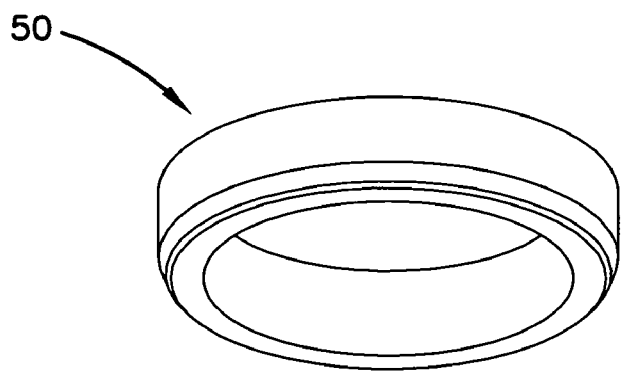
FIG. 13 is a perspective view of a retainer of the orthopedic fixation device of FIG. 1.

Referring to FIG. 13, the retainer 50 (e.g., a ring) of the orthopedic fixation device 10 of FIG. 1 is shown. The ring 50 is adapted to be coupled (e.g., welded, bonded, swaged, snap-fit, threaded, press-fit or otherwise secured) to the bottom of the receiver 30 after the seat structure 40 and the head 23 of the screw 20 have been inserted within the receiver 30. The ring 50, once coupled, captures and retains the head 23 of the screw 20 within the bottom portion of the receiver 30 (see FIGS. 3 and 4). The retainer 50 includes an annular seating surface 50a that faces in a generally upward direction an includes a curvature that generally complements the curvature of the exterior of the screw head 23. The seating surface 50a is adapted to provide substantially full ring contact 82 (shown in FIG. 4B) with the head 23 of the screw 20 regardless of the angular orientation of the screw 20 relative to the receiver 30. In this manner, when the setscrew 70 is fully tightened, the seating surface 44a of the seat structure 40 and the seating surface 50a of the ring 50 cooperate to provide two substantially full rings of contact 80 and 82 (shown in FIGS. 4A and 4B) between which the spherical head 23 of the screw 20 is captured and clamped to lock the head 23 at a desired angular position relative to the receiver 30.

In use, the setscrew 70 provides an axial locking force on the rod 60. When contacted by the setscrew 70, the rod 60 is caused to axially apply a force on the seat structure 40. The seat structure 40, in turn, moves to create a clamping effect on the spherical head 23 of the bone screw 20 against the ring 50 coupled to the bottom end 31 of the receiver 30. When the setscrew 70 is fully tightened, the rod 60 is locked between the setscrew 70 and the seat structure 40, and the screw head 23 is locked between the seat structure 40 and the retainer 50.

As illustrated in FIGS. 3 and 4, the setscrew 70 may include a curved bottom surface 71. With this configuration, the setscrew 70 contacts the rod 60 at a single point of contact 73. This feature provides stability to a rod that has been bent upwardly when it is seated on the top seat 42 of the seat structure 40. The threads 72 of the setscrew 70 can also be designed with a double lead to allow the setscrew 70 to start more easily than with a single lead. Torque for driving the setscrew 70 can be provided by a tool (e.g., a torque wrench) inserted into sockets 74 (e.g., hex-sockets) provided in the setscrews 70.

Figure 14:
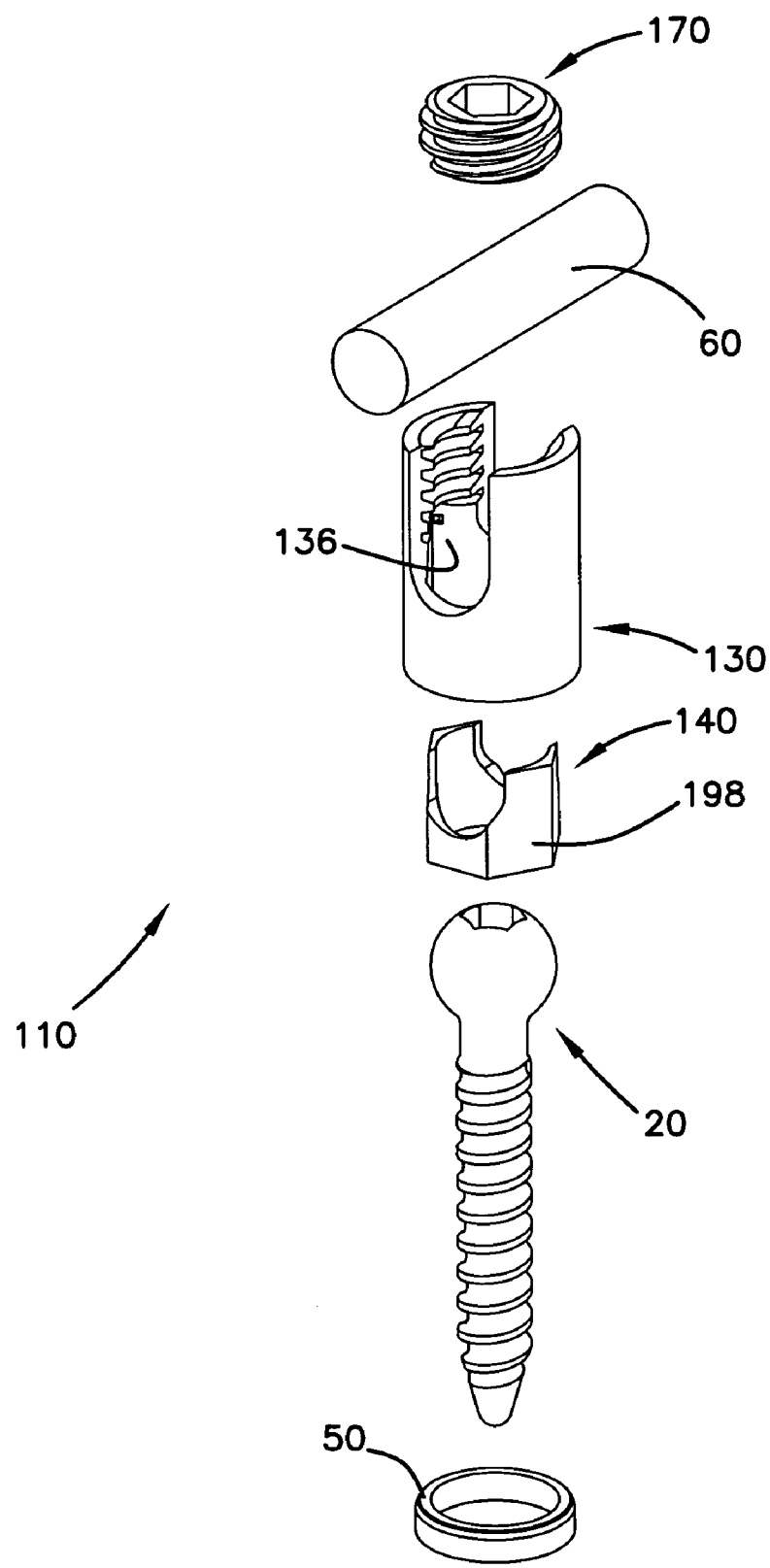
FIG. 14 is an exploded perspective view of a second embodiment of an orthopedic fixation device having features that are examples of inventive aspects in accordance with the principles of the present disclosure.
Figure 15:
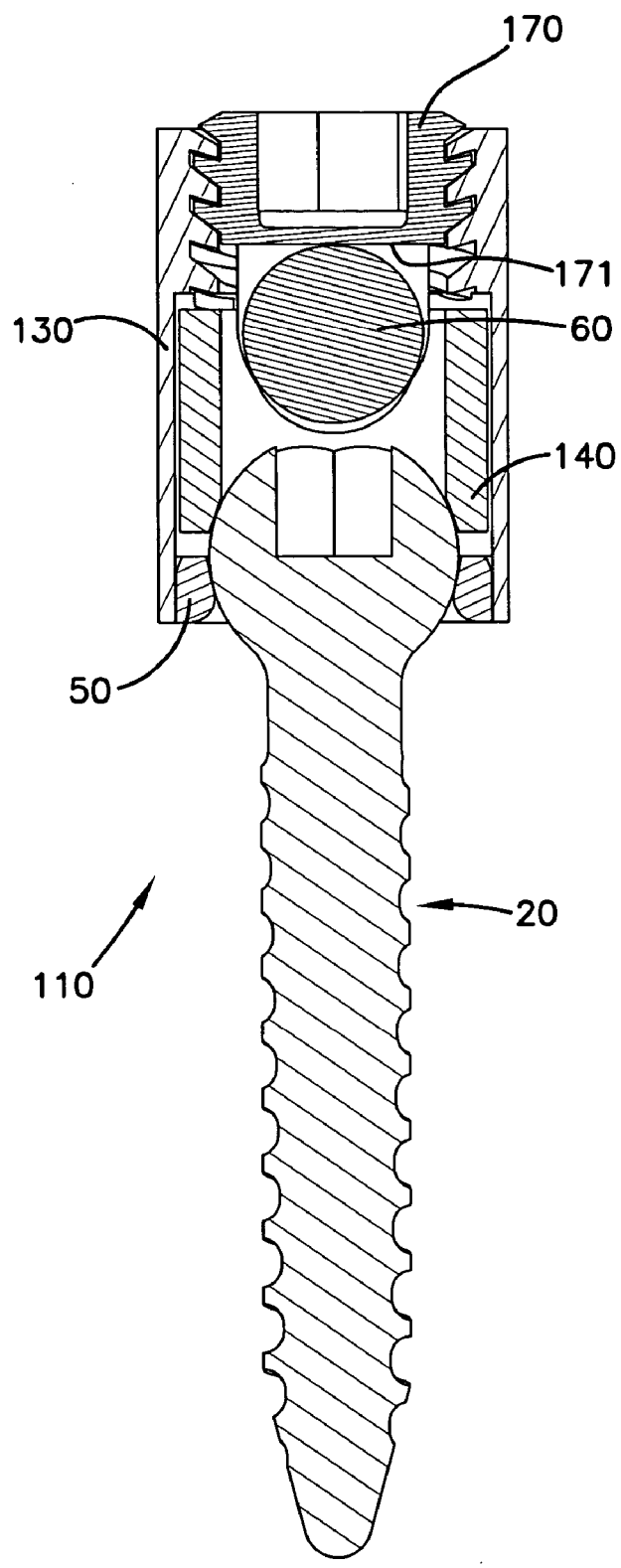
FIG. 15 is a cross-sectional view of the orthopedic fixation device of FIG. 14 taken along a vertical cross-sectional plane that bisects the device, the device is shown assembled with a rod secured within a receiver of the device.

FIGS. 14 and 15 illustrate a second embodiment of orthopedic fixation device 110 having features that are examples of inventive aspects in accordance with the principles of the present disclosure. The orthopedic fixation device 110 includes a seat structure 140. The seat structure 140 is similar to the embodiment of FIG. 1, except that the seat structure 140 includes an exterior surface 198 of a hexagonal cross-sectional profile. The device 110 also includes a receiver 130 with an internal hexagonal cross-sectional shape 136 configured to match the shape of the exterior 198 of the seat structure 140. The matching shapes provide a keying function to ensure the seat structure 140 is inserted into the receiver 130 at the appropriate rotational orientation, and also limit the rotation of the seat structure 140 within the receiver 130. The device 110 also includes a setscrew 170 having a flat bottom surface 171 for contacting the rod 60 when the rod is clamped within the device 110.

Figure 16:
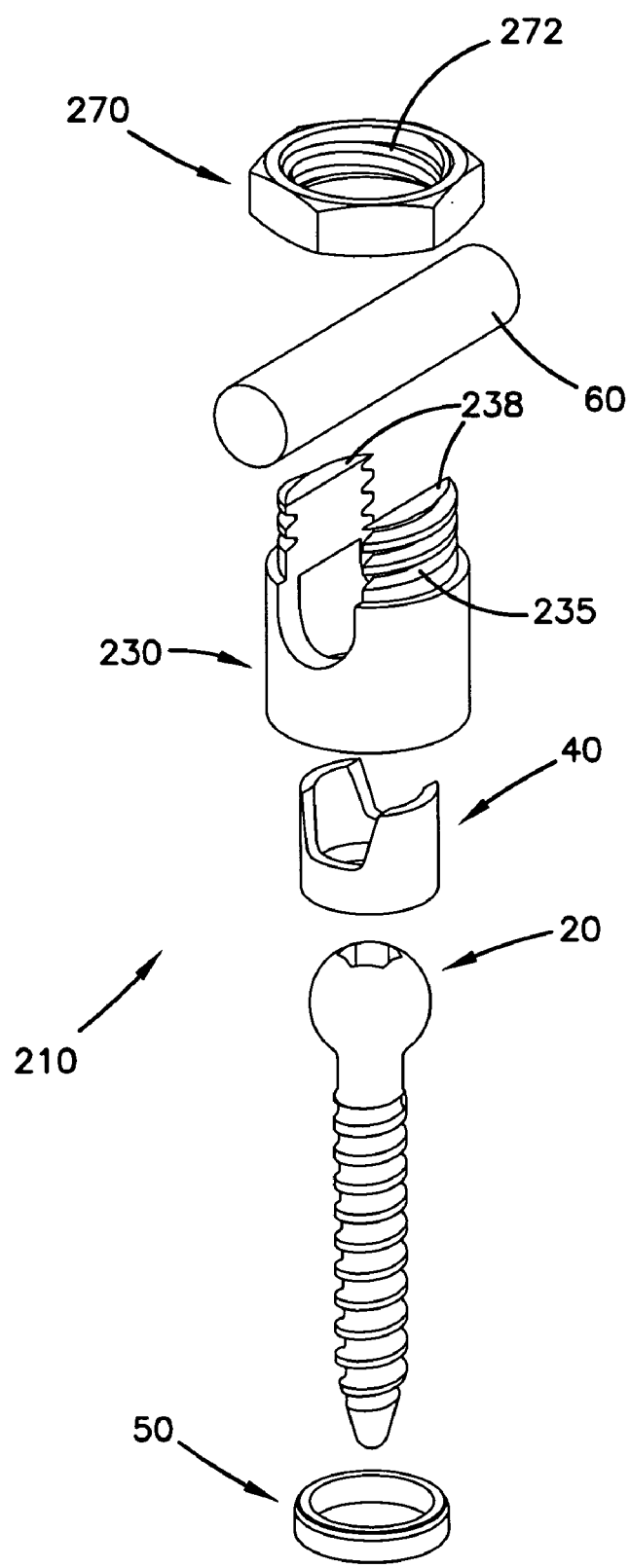
FIG. 16 is an exploded perspective view of a third embodiment of an orthopedic fixation device having features that are examples of inventive aspects in accordance with the principles of the present disclosure.
Figure 17:
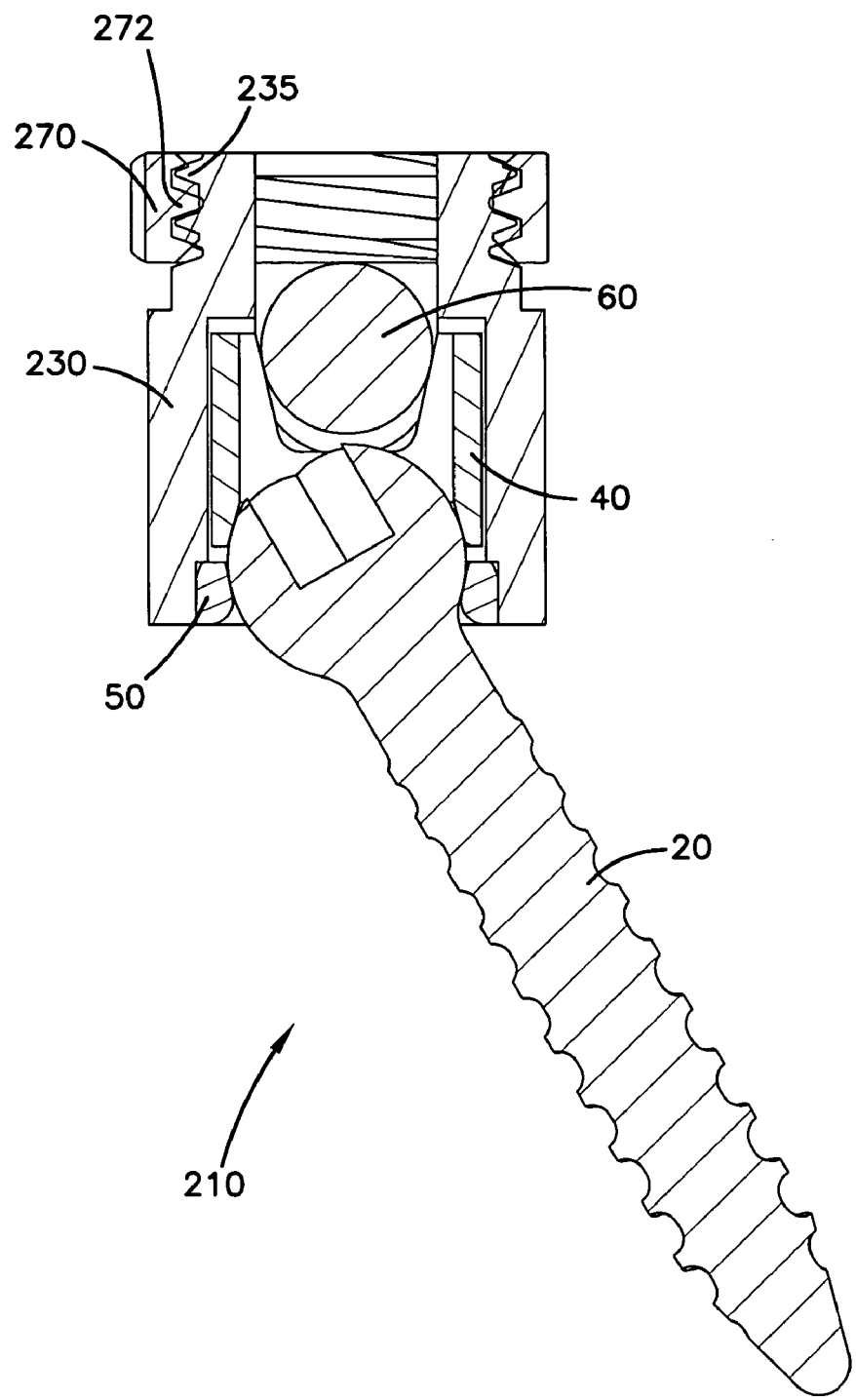
FIG. 17 is a cross-sectional view of the orthopedic fixation device of FIG. 16 taken along a vertical cross-sectional plane that bisects the device, the device is shown assembled with a rod secured within a receiver of the device.
Figure 24:
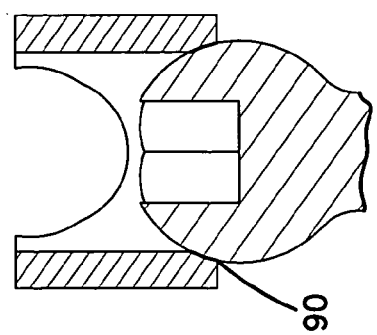
FIG. 24 is a cross-sectional view of still another embodiment of a seat having a modified surface for seating the anchor head.
Figure 23:
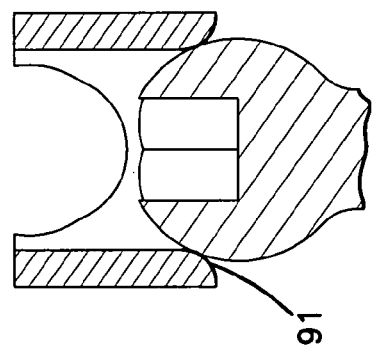
FIG. 23 is a cross-sectional view of a further embodiment of a seat having a modified surface for seating the anchor head.
Figure 22:
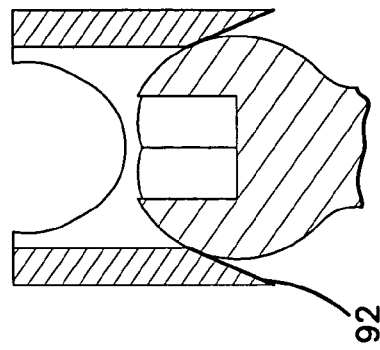
FIG. 22 is a cross-sectional view of another embodiment of a seat having a modified surface for seating the anchor head.
Figure 21:
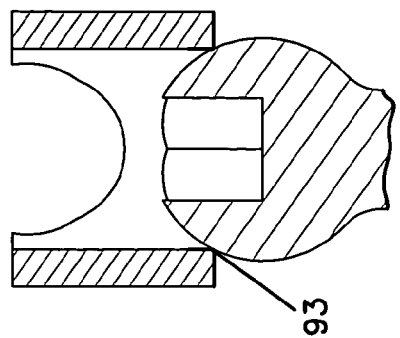
FIG. 21 is a cross-sectional view of the seat of the orthopedic fixation device of FIG. 1, an anchor head is shown seated at the bottom of the seat.

FIGS. 16 and 17 illustrate a third embodiment of orthopedic fixation device 210 having features that are examples of inventive aspects in accordance with the principles of the present disclosure. The device 210 is similar to the embodiment of FIG. 1, except has been modified to include a different top locking arrangement. The locking arrangement of the fixation device 210 includes a fastener in the form of a lock nut 270 that mounts on a receiver 230. The lock nut 270 is adapted to be threaded about the exterior of legs 238 of the receiver 230. The receiver 230 includes external threads 235 adapted to mate with internal threads 272 of the nut 270. The nut 270 can also be designed with a double lead as previously discussed for the set screw type of a locking mechanism to facilitate start-up.

The embodiments of the locking arrangements disclosed herein (e.g., the set screw 70 and the nut 270) are merely examples of types of locking arrangements that can be used. The locking arrangements can include any mechanism adapted to provide an axial locking force on the rod 60 to cause it to provide a force on the seat structure 40, thereby, causing it to move and create a clamping effect on the spherical head 23 of the bone screw 20 against the retainer 50. Example structures include lock nuts, screws, collars, plugs, sleeves, tapered sleeves, tapered plugs or other structures. Torque or non-torque locking mechanisms may be utilized for the orthopedic fixation system.

The rod seat 42 of the seat structure 40 is preferably generally U-shaped as shown in FIG. 18. However, the shape can be varied. For example, FIG. 19 shows a seat structure 340 having a truncated V-shaped seat 342. FIG. 20 shows a seat structure 440 having a rod seat 442 formed by opposing legs 443. The seat structure 440 also includes provisional retaining tabs 400 adapted to provisionally retain the rod 60 between the legs 443 after the rod 60 is snapped past the tabs 400 during insertion. In this embodiment, the legs 443 are adapted to deflect (e.g. flex apart) to accommodate the rod 60 and then move inwardly back toward the non-deflected orientation such that the tabs 400 provisionally retain the rod 60 within the seat. When provisionally retained, the position of the rod can be readily adjusted. To remove the rod 60 from the pocket, the rod 60 is pulled upwardly with sufficient force to cause the legs 443 to deflect back apart thereby enabling the rod to pass between the tabs 400. A fastener such as a lock nut, set screw or other fastener can be used to finally lock the rod within the seat structure once the rod has been adjusted to its final position.

To increase the contact surface and/or to vary the stresses between the bottom seat 44 of the seat structure 40 and the head 23 of the screw 20, the seat/spherical head interface may include various cross-sectional shapes. For example, as shown in FIGS. 21-24, the bottom seat may include a cupped cross-sectional shape 90, a rounded cross-sectional shape 91, a tapered cross-sectional shape 92 and a squared cross-sectional shape 93, respectively, at the seat/head interface. The bottom seat may also include a cross-sectional shape at the seat/head interface that is made up of a combination of the shapes discussed.

The various components of the devices disclosed herein (e.g., the receivers, fasteners, anchors, retainers and seat structures) can be made of any number of different types of biocompatible materials. Example materials include materials such as Titanium, Nitinol, Stainless Steel, Thermoplastic polymers, Thermoset polymers as well as other materials.

As shown in the various embodiments depicted herein, the anchors of the fixation devices have been depicted as bone screws. In other embodiments, the anchors can include hooks, pins, expandable anchors, barbed anchors or other structures.

From the foregoing detailed description, it will be evident that modifications and variations can be made in the devices of the invention without departing from the spirit or scope of the invention. Therefore, it is intended that all modifications and variations not departing from the spirit of the invention come within the scope of the claims and their equivalents.

I claim:

1. An orthopedic fixation device comprising:
a receiver including first and second legs and a first pocket defined between the legs;
a rod having a curved portion;
an anchor including a head; and
a seat structure that mounts within the receiver, the seat structure including a top seat for receiving the rod and a bottom seat for receiving the head of the anchor, the top seat including first and second legs extending from a base of the top seat, the top seat including an interior defining a second pocket between the first and second legs configured to receive the rod therethrough;
the first leg of the seat structure having first and second raised ridges and a recessed portion extending between the first raised ridge and the second raised ridge facing the interior of the top seat, the recessed portion of the first leg extending to the topmost extent of the first and second raised ridges of the first leg, each ridge including a discrete rod contact location disposed along a planar portion of the raised ridge for contacting the rod, and a rod non-contact area defined by the recessed portion of the first leg spaced from the rod;

the second leg of the seat structure having first and second raised ridges and a recessed portion extending between the first raised ridge and the second raised ridge facing the interior of the top seat, the recessed portion of the second leg extending to the topmost extent of the first and second raised ridges of the second leg, each ridge including a discrete rod contact location disposed along a planar portion of the raised ridge for contacting the rod, and a rod non-contact area defined by the recessed portion of the second leg spaced from the rod;

wherein the first raised ridge of the first leg deviates from the recessed portion of the first leg to extend toward the first raised ridge of the second leg, and the first raised ridge of the second leg deviates from the recessed portion of the second leg to extend toward the first raised ridge of the first leg, retaining a distance across the second pocket between the first raised ridge of the first leg and the first raised ridge of the second leg;

wherein the second raised ridge of the first leg deviates from the recessed portion of the second leg to extend toward the second raised ridge of the second leg, and the second raised ridge of the second leg deviates from the recessed portion of the second leg to extend toward the second raised ridge of the first leg, retaining a distance across the second pocket between the second raised ridge of the first leg and the second raised ridge of the second leg;

wherein a distance across the second pocket from the recessed portion of the first leg to the recessed portion of the second leg is greater than the distance across the second pocket between the first raised ridge of the first leg and the first raised ridge of the second leg;

wherein the distance across the second pocket from the recessed portion of the first leg to the recessed portion of the second leg is greater than the distance across the second pocket between the second raised ridge of the first leg and the second raised ridge of the second leg; and wherein the seat structure is configured such that the rod is spaced from the base of the top seat when the rod is received in the second pocket and in contact with each of the discrete rod contact locations of the seat structure;

wherein the curved portion of the rod is disposed within the top seat such that the rod has a lateral curvature such that the rod curves toward the first leg of the receiver and curves away from the second leg of the receiver.

2. An orthopedic fixation device according to claim 1, wherein the receiver includes a top and a bottom end and wherein the anchor is loaded through the bottom end of the receiver.

3. An orthopedic fixation device according to claim 1, wherein the bottom seat provides substantially full ring contact with the head of the anchor regardless of the orientation of the anchor relative to the receiver.

4. An orthopedic fixation device according to claim 2, wherein a ring is secured to the bottom end of the receiver to secure the head of the anchor within the receiver.

5. An orthopedic fixation device according to claim 4, wherein the ring provides substantially full ring contact with the head of the anchor regardless of the orientation of the anchor relative to the receiver.

6. An orthopedic fixation device according to claim 1, wherein the receiver includes a keying feature for limiting rotation of the seat structure relative to the receiver prior to the rod being secured to the device, the keying feature including an exterior-shape of the seat structure and an interior-shape of the receiver, wherein the exterior-shape of the seat structure matches the shape of the interior-shape of the receiver.

7. An orthopedic fixation device according to claim 2, wherein the seat structure is loaded through the bottom end of the receiver.

8. An orthopedic fixation device according to claim 1, further comprising a locking mechanism for securing the rod within the receiver.

9. An orthopedic fixation device according to claim 8, wherein the locking mechanism includes a set screw threaded into the pocket of the receiver.

10. An orthopedic fixation device comprising:
a receiver including two legs and a first pocket defined between the legs;
a rod having a curved portion;
an anchor including a head;
a seat structure that mounts within the receiver, the seat structure including a top seat for receiving the curved portion of the rod and a bottom seat for receiving the head of the anchor;
the top seat including first and second legs extending from a base of the top seat, the top seat including an interior defining a second pocket between the first and second legs configured to receive the rod therethrough;
the first leg of the seat structure having first and second raised ridges and a recessed portion extending between the first raised ridge and the second raised ridge facing the interior of the top seat, the recessed portion of the first leg extending to the topmost extent of the first and second raised ridges of the first leg, each ridge including a discrete rod contact location disposed along a planar portion of the raised ridge for contacting the rod, and a rod non-contact area defined by the recessed portion of the first leg spaced from the rod;
the second leg of the seat structure having first and second raised ridges and a recessed portion extending between the first raised ridge and the second raised ridge facing the interior of the top seat, the recessed portion of the second leg extending to the topmost extent of the first and second raised ridges of the second leg, each ridge including a discrete rod contact location disposed along a planar portion of the raised ridge for contacting the rod, and a rod non-contact area defined by the recessed portion of the second leg spaced from the rod;
wherein the first raised ridge of the first leg deviates from the recessed portion of the first leg to extend toward the first raised ridge of the second leg, and the first raised ridge of the second leg deviates from the recessed portion of the second leg to extend toward the first raised ridge of the first leg, retaining a distance across the second pocket between the first raised ridge of the first leg and the first raised ridge of the second leg;
wherein the second raised ridge of the first leg deviates from the recessed portion of the second leg to extend toward the second raised ridge of the second leg, and the second raised ridge of the second leg deviates from the recessed portion of the second leg to extend toward the second raised ridge of the first leg, retaining a distance across the second pocket between the second raised ridge of the first leg and the second raised ridge of the second leg;
wherein a distance across the second pocket from the recessed portion of the first leg to the recessed portion of the second leg is greater than the distance across the second pocket between the first raised ridge of the first leg and the first raised ridge of the second leg; and
wherein the distance across the second pocket from the recessed portion of the first leg to the recessed portion of the second leg is greater than the distance across the second pocket between the second raised ridge of the first leg and the second raised ridge of the second leg;

wherein the seat structure is configured such that the rod is spaced from the base of the top seat when the curved portion of the rod is received in the second pocket and in contact with each of the discrete rod contact locations of the seat structure, the curved portion of the rod curving laterally with a concave curvature facing the first leg and a convex curvature facing the second leg;

a ring secured to the receiver such that the head of the anchor is captured between the ring and the bottom seat of the seat structure;

the bottom seat providing substantially full ring contact with the head of the anchor throughout a range of pivotal movement of the anchor relative to the receiver; and the ring providing substantially full ring contact with the head of the anchor throughout a range of pivotal movement of the anchor relative to the receiver.

11. An orthopedic fixation device according to claim 10, wherein the receiver includes a top and a bottom end and wherein the anchor is loaded through the bottom end of the receiver.

12. An orthopedic fixation device according to claim 10, wherein the receiver includes a keying feature for limiting rotation of the seat structure relative to the receiver, the keying feature including an exterior-shape of the seat structure and an interior-shape of the receiver, wherein the exterior-shape of the seat matches the shape of the interior-shape of the receiver.

13. An orthopedic fixation device according to claim 11, wherein the seat structure is loaded through the bottom end of the receiver.

14. An orthopedic fixation device according to claim 10, further comprising a locking mechanism for securing the rod within the receiver.

15. An orthopedic fixation device according to claim 14, wherein the locking mechanism includes a set screw threaded into the pocket of the receiver.

16. An orthopedic fixation system comprising:
a rod including a curved section;
an anchor including a head;
a receiver including two legs and a first pocket defined between the legs;
a seat structure that mounts within the receiver, the seat structure including a top seat for receiving the curved section of the rod and a bottom seat for receiving the head of the anchor;
the top seat including first and second legs extending from a base of the top seat, the top seat including an interior defining a second pocket between the first and second legs configured to receive the rod therethrough;
the first leg of the seat structure having first and second raised ridges and a recessed portion extending between the first raised ridge and the second raised ridge facing the interior of the top seat, the recessed portion of the first leg extending to the topmost extent of the first and second raised ridges of the first leg, each ridge including a discrete rod contact location disposed along a planar portion of the raised ridge for contacting the rod, and a rod non-contact area defined by the recessed portion of the first leg spaced from the rod;
the second leg of the seat structure having first and second raised ridges and a recessed portion extending between the first raised ridge and the second raised ridge facing the interior of the top seat, the recessed portion of the second leg extending to the topmost extent of the first and second raised ridges of the second leg, each ridge including a discrete rod contact location disposed along a planar portion of the raised ridge for contacting the rod, and a rod non-contact area defined by the recessed portion of the second leg spaced from the rod;

wherein the first raised ridge of the first leg deviates from the recessed portion of the first leg to extend toward the first raised ridge of the second leg, and the first raised ridge of the second leg deviates from the recessed portion of the second leg to extend toward the first raised ridge of the first leg, retaining a distance across the second pocket between the first raised ridge of the first leg and the first raised ridge of the second leg;

wherein the second raised ridge of the first leg deviates from the recessed portion of the second leg to extend toward the second raised ridge of the second leg, and the second raised ridge of the second leg deviates from the recessed portion of the second leg to extend toward the second raised ridge of the first leg, retaining a distance across the second pocket between the second raised ridge of the first leg and the second raised ridge of the second leg;

wherein a distance across the second pocket from the recessed portion of the first leg to the recessed portion of the second leg is greater than the distance across the second pocket between the first raised ridge of the first leg and the first raised ridge of the second leg; and wherein the distance across the second pocket from the recessed portion of the first leg to the recessed portion of the second leg is greater than the distance across the second pocket between the second raised ridge of the first leg and the second raised ridge of the second leg;

wherein the seat structure is configured such that the rod is spaced from the base of the top seat when the curved section of the rod is received in the second pocket and in contact with each of the discrete rod contact locations of the seat structure such that an edge having an inner concave radius of curvature of the curved section faces towards the first leg and contacts the first and second ridges of the first leg and an edge having an outer convex radius of curvature of the curved section faces toward the second leg and contacts the first and second ridges of the second leg;

a ring secured to the receiver such that the head of the anchor is captured between the ring and the bottom seat of the seat structure;

the bottom seat providing substantially full ring contact with the head of the anchor throughout a range of pivotal movement of the anchor relative to the receiver;

the ring providing substantially full ring contact with the head of the anchor throughout a range of pivotal movement of the anchor relative to the receiver; and the receiver including a keying feature for limiting rotation of the seat structure relative to the receiver, the keying feature including an exterior-shape of the seat structure and an interior-shape of the receiver, wherein the exterior-shape of the seat structure matches the shape of the interior-shape of the receiver.

17. The orthopedic fixation device according to claim 1, wherein the discrete rod contact locations are aligned generally perpendicular to the longitudinal axis of the rod and the seat structure.

18. The orthopedic fixation device according to claim 10, wherein the discrete rod contact locations are aligned generally perpendicular to the longitudinal axis of the rod and the seat structure.

19. The orthopedic fixation system according to claim 16, wherein the discrete rod contact locations are aligned generally perpendicular to the longitudinal axis of the rod and the seat structure.

* * * * *